United States Patent [19]

Beardsmore et al.

[11] 4,402,831
[45] Sep. 6, 1983

[54] EFFLUENT TREATMENT

[75] Inventors: Andrew J. Beardsmore, Guisborough; Keith A. Powell, Yarm, both of England

[73] Assignee: Imperial Chemical Industries PLC, London, England

[21] Appl. No.: 356,805

[22] Filed: Mar. 10, 1982

[30] Foreign Application Priority Data

Mar. 20, 1981 [GB] United Kingdom ............... 8108774

[51] Int. Cl.³ .............................................. C02F 3/34
[52] U.S. Cl. .................................. 210/606; 210/611; 210/632; 210/904; 435/262
[58] Field of Search ............... 210/632, 904, 606, 612, 210/611, 602; 435/128, 177, 262, 171

[56] References Cited

U.S. PATENT DOCUMENTS 3,926,795 12/1975 Saldick ............................ 210/904
3,940,332 2/1976 Kato et al. ....................... 210/611
4,321,327 3/1982 Chen et al. ...................... 435/177

FOREIGN PATENT DOCUMENTS 43-28592 12/1968 Japan .................................. 210/904
54-71856 6/1979 Japan .................................. 210/611
2006741 5/1979 United Kingdom ............... 210/904
2025919 1/1980 United Kingdom ............... 210/611

OTHER PUBLICATIONS

Chemical Abstracts; vol. 69; 5065j, (1968).
Fry, W. E. et al., Cyanide Degradation by an Enzyme from *Stemphylium Loti;* Archives of Biochemistry and Biophysics, vol. 151, pp. 468–474, (1972).
Nazly, N. et al., "Cyanide Degradation of Immobilized Fungi"; *Biotechnology Letters,* vol. 3, No. 7, pp. 363–368, (Jul. 1981).
Fry, W. E. et al., "Development of Cyanide Tolerance in Stemphylium Loti"; *Phytopathology,* vol. 67, pp. 1001–1006, (1977).

*Primary Examiner*—Benoît Castel
*Attorney, Agent, or Firm*—Cushman, Darby & Cushman

[57] ABSTRACT

Cyanide degrading fungi are grown in the mycalial form. The mycelium is then immobilized and the immobilized mycelium used to degrade cyanide ion in cyanide containing effluents. At least 95% of the cyanide ion is degraded.

6 Claims, No Drawings

EFFLUENT TREATMENT

This invention relates to effluent treatment and in particular to the degradation of cyanide containing effluents.

Because of the toxicity of inorganic cyanide, treatment of cyanide containing aqueous effluents is necessary before the effluent can safely be discharged into bodies of water such as rivers, lakes and estuaries.

While cyanide containing effluents can be treated chemically, e.g. by oxidation with hypochlorite this tends to be expensive. One microbiological method that has been proposed involves anaerobic digestion followed by aerobic digestion (see U.S. Pat. No. 3,145,166).

It is also known that certain microorganisms, particularly certain fungi, are capable of degrading cyanide to formamide by means of an enzyme formamide hydrolyase, otherwise termed cyanide hydratase, (for example see Archives of Biochemistry and Biophysics 151 (1972) pages 468 to 474, and Phytopathology 67 (1977) pages 1001 to 1006).

We have found that fungal mycelia containing cyanide hydratase can be immobilised and the resulting immobilised mycelium retains sufficient enzyme activity to be of use for treating cyanide-containing effluents with substantially complete degradation of the cyanide.

Accordingly we provide a process for the degradation of inorganic cyanides in effluents comprising contacting the effluent with an immobilised fungal mycelium containing cyanide hydratase for sufficient time to degrade at least 95% of the cyanide ions in the effluent.

Fungi that may be used include *Stemphylium loti*, e.g. ATCC 11718; *Mycoleptodiscus terrestris*, e.g. CBS 231.53; *Fusarium moniliforme*, e.g. No. 3104.SA.49a available from the Canadian Department of Agriculture, Culture Collection, Ottawa, and which has also been deposited as CBS 161.82; *Helminthosporium sorghicola*, otherwise known as *Drechslera sorghicola*, e.g. CBS 249.49; *Periconia circinata*, e.g. CBS 263.37; and *Glomerella tucamanensis*, e.g. CBS 132.37. (ATCC No. refers to the number designated by the American Type Culture Collection, 12301 Park Lawn Drive, Rockville, Md. 20852, USA, while CBS No. refers to the number designated by the Central Bureau Voor Schimmelcultures, Baarn, Netherlands). Other fungi that may be used and which have been described in the literature as producing the enzyme include *Collectotrichum graminicola, Gloeocercospora sorghi, Helminthosphorium turcicum, H. maydis, H. carbonum, H. victoriae,* and *Phoma*.

Fungi can be made to grow in two distinct forms, namely a ball or pellet form or in a mycelial form where the fungal cells are diffuse filamentous strands dispersed in the growth medium. It is important that the fungus is grown in the mycelial, as opposed to ball or pellet, form since, after immobilisation, little diffusion of the effluent can occur into the fungal pellet or ball, and so a great deal of the active enzyme within the immobilised ball or pellet is not efficiently utilised.

Often when growing fungi, the ball or pellet form is obtained: however adjustment of the growth conditions, particularly the following parameters:
  pH,
  nitrogen source (nature and amount),
  carbon source (nature and amount),
  amount of phosphorus source, will enable the mycelial form to be obtained. Thus with any particular micro-organism, simple experimentation varying the above parameters will enable the mycelial form to be obtained.

The preferred carbon sources are carbohydrates, particularly glucose.

When the desired concentration of mycelium has been achieved, the enzyme cyanide hydratase may be induced by adding to the culture a low concentration of cyanide ions, e.g. 0.05 to 5, preferably 0.1 to 1 mM per gram of cells (dry weight) and continuing culturing for 1 to 24, preferably about 12, hours at 20° to 40° C.

The immobilised mycelium may be obtained by flocculating the culture with a polyelectrolyte flocculating agent, for example as described in United Kingdom Patent Specification 1368650, optionally followed by freezing or drying the flocculated mycelium. Other methods of immobilisation of the mycelium include entrapment of the harvested mycelium in a suitable material such as polyacrylamide, an alginate or carrageenan; treatment of the mycelium with an adhesive material such as glutaraldehyde before or after harvesting; and drying the harvested mycelium, preferably after treatment of the mycelium with an adhesive material as described above. The immobilised mycelium may be converted into a suitable particulate form for packing into beds or columns by extrusion, granulation and/or milling.

When immobilising using polyelectrolyte flocculating agents, e.g. a mixture of cationic and anionic flocculating agents, such as 'Primafloc' C7 and 'Primafloc' A10 (made by Rhom and Haas, Philadelphia), the amount of each flocculating agent employed is normally of the order of 4% by weight, based on the cell dry weight. The use of amounts of flocculating agents in a large excess over that required to achieve flocculation is desirably avoided, as such large amounts may give relatively tightly bound particles into which the effluent cannot readily diffuse, thus preventing efficient utilisation of the enzyme in the cells within the particles.

The acitivity of the flocculated particles can be increased by dry milling. However the particles should not be milled to too small a size as then the pressure drop required to cause the effluent to flow through the treatment bed or column becomes uneconomically large. For this reason the greatest dimension of the particles is preferably above 1.5 mm.

An immobilization technique that gives greater activity involves entrapment of the mycelium in a polyacrylamide (see for example J. Ferment. Technol. 53 (1975), 6, p 380-385) or alginate (see for example Biotechnol. Bioeng. 19 (1977) p 387-397). A particularly suitable technique is to prepare a mixture of the fungal dispersion and a solution of an alginate, and then to add this mixture, in dropwise fashion, to a solution, preferably buffered, of a precipitant such as a solution containing calcium ions. Calcium alginate is thus precipitated entrapping the mycelium.

The immobilised mycelium is then packed into beds or columns wherein it is contacted with the effluent. Cyanide wastes from chemical plants often are highly alkaline, e.g. having a pH of at least about 10. For efficient operation the pH is preferably adjusted to between 7 and 10 before contact with the immobilised mycelium.

The temperature at which the effluent is treated by the immobilised mycelium is preferably within the range 0 to 40, particularly 0° to 30° C. Low temperatures, e.g. 4° C., tend to prolong the period over which the enzyme is active.

The contact time between the immobilised mycelium and the effluent will depend on the cyanide content of the effluent, the desired final cyanide content, and the proportions of immobilised mycelium to effluent. The maximum rate of cyanide ion degradation will also depend on the proportion of active enzyme in the mycelium. Generally the maximum rate will lie within the range 0.5 to 25 g cyanide ion per g mycelium per hour.

In the process of the invention, the effluent treatment is continued until at least 95%, and in particular at least 98% of the cyanide have been degraded: the proportion of cyanide ions that should be degraded will of course depend on the initial, and desired final, cyanide ion concentration. For discharge into rivers or other bodies of water, the concentration of cyanide ions in the discharged effluent is preferably below 10 parts per million (ppm) by weight.

The immobilised mycelium will require replacement upon exhaustion of cyanide hydratase activity. The replenishment of the immobilised mycelium may be conducted on a continuous or intermittent basis. In general, the weight of cyanide ion that can be treated is over about 200 times the weight of the immobilised mycelium before exhaustion of the cyanide hydratase activity.

Because of the need to replenish spent immobilised mycelium, the effluent is preferably treated by passage through a series of beds or columns and the columns or beds are replenished with fresh immobilised mycelium in rotation.

For economic operation and in order to achieve the desired residence time and acceptable flow rates of effluent, the bed volume occupied by the immobilised mycelium may be increased from the volume occupied by the mycelium itself by incorporation of an inert particulate material such as dolomite or silica into the immobilised mycelium preparation.

The invention is of particular use in treating effluents from cyanide producing or utilising chemical plants. It is also of use in treating cyanide containing effluents from an extraction or metal working plants e.g. electroplating works.

The enzyme does not appear to be inhibited by metal ions. However metals are often complexed with the cyanide. In general such complexes are not degraded by the enzyme. Some such complexes are non-toxic and so do not require degradation. Some complexes can be broken down, e.g. by alkali treatment, and the metals recovered, if desired, by passage through an ion exchange column before or after degradation of the cyanide by means of the present invention.

The invention is illustrated by the following examples in which all parts and percentages are expressed by weight.

EXAMPLE 1

A mycelium of *Stemphylium loti* (ATCC 11718) was grown and cyanide hydratase induced by adding a small concentration of cyanide to the culture and continuing culturing for 2 hours. The mycelium was immobilised by flocculation, harvesting the flocculated mycelium, and drying. 10 mg of the immobilised mycelium was placed in a shake flask with 100 ml of water containing 2500 ppm of cyanide ions buffered to a pH of about 7.5. After 12 hours at 28° C. the cyanide ion concentration was about 100 ppm. The aqueous solution was then decanted from the immobilised cells into a second shake flask to which another 10 mg of the immobilised mycelium was added. After a further 6 hours at 28° C. the cyanide ion concentration was below 10 ppm.

EXAMPLE 2

A cell suspension of *Fusarium moniliforme* (obtained from the Canadian Department of Agriculture Culture Collection, Ottawa, under No. 3104.SA.49a) was prepared from an agar slant and inoculated into 50 ml of medium A and incubated, with shaking, at 28° C. for 3 days. 10 ml of the resulting culture was transferred to 200 ml of medium A in a flask and incubated, with shaking, at 28° C. for 28 hours. The organism grew in the mycelial form.

Cyanide hydratase was then induced by adjusting the pH to 7.5 and adding hydrogen cyanide to a concentration of 1 m Molar, and incubating for 12 hours at 28° C.

Medium A, which had a pH of 5.8–5.7 had the following composition:

| | |
|---|---|
| glucose | 30 g |
| $KH_2PO_4$ | 5 g |
| casitone | 2.1 g |
| $MgSO_4.7H_2O$ | 1 g |
| Yeast extract | 1 g |
| KCl | 0.5 g |
| Medium B | 1 ml |
| Distilled water | to make up to 1 liter |

Medium B had the following composition, per liter of distilled water:

| | |
|---|---|
| $FeSO_4.7H_2O$ | 1 g |
| $ZnSO_4.7H_2O$ | 1 g |
| $CuSO_4.5H_2O$ | 0.15 g |
| $MnSO_4.4H_2O$ | 0.1 g |
| $K_2MoO_4$ | 0.1 g |
| HCl (concentrated) | sufficient to just give a clear solution. |

The mycelium containing the induced cyanide hydratase was harvested by centrifugation at 10000 g for 10 minutes.

EXAMPLE 3

1.75 parts (dry weight) of the mycelium obtained in Example 2 was incubated at 20° C. in 1000 parts of an aqueous solution containing 2.75 parts of potassium cyanide at pH 8.5. (The solution thus contained 1300 ppm of cyanide ion). After 60 minutes incubation, the cyanide ion concentration was below 10 ppm; i.e. over 99% of the cyanide ion had been degraded.

EXAMPLE 4

The procedure of Examples 2 and 3 was repeated using medium C in place of medium A. Medium C had the following composition:

| | | |
|---|---|---|
| Molasses | 50 | g |
| Phosphate buffer pH 7.2 | 20 | ml |
| 36% Ammonium Sulphate solution | 5 | ml |
| 40% Magnesium Sulphate solution | 0.5 | ml |
| Ferric chloride | 0.1 | ml |
| Medium B | 1 | ml |
| Distilled water | 975 | ml |

The organism grew in the pelleted form. The activity, i.e. rate of cyanide degradation per unit amount of the organism, of the enzyme was only about 20% of that of the mycelial cells of Example 3.

EXAMPLE 5

The procedure of Examples 2 and 3 was repeated using
 (i) medium D
 (ii) medium E
 (iii) medium F in place of medium A. In each case a mixture of mycelial and pelleted growth was obtained and the enzyme activity was less than that of the wholly mycelial-form cells of Example 3.

The compositions of the media D, E and F, were as follows:

|  | D | E | F |
|---|---|---|---|
| glycerol | 20 g | — | — |
| glucose | — | 25 g | — |
| sucrose | — | — | 40 g |
| bacteriological peptone | 10 g | — | — |
| yeast extract | 5 g | 3 g | — |
| tryptone | — | 5 g | — |
| corn steep liquor | — | — | 5 g |
| $KH_2PO_4$ | 5 g | — | 5 g |
| $MgSO_4.7H_2O$ | — | — | 1 g |
| Medium B | — | — | 2 ml |
| Distilled water | to 1 liter | to 1 liter | to 1 liter |

EXAMPLE 6

Example 2 was repeated and 100 parts of the harvested mycelium were suspended in 300 parts of 0.1 M Tris. HCl buffer (pH 8.5). A 2% solution of 'Primafloc' C7 (supplied by Rohm and Haas) at pH 7.0 was added, with continuous stirring, until the cells flocculated. Then an equal amount of a 2% solution of 'Primafloc' A10 (supplied by Rohm and Haas) at pH 6.8 was added. The total amount of each polyelectrolyte flocculating agent added was about 4% of the cell dry weight. The flocculated cells were harvested by filtration, using a Whatman No. 1 filter, and then extruded through a 2 mm aperture. The extruded, wet, immobilised cells were then cut into particles of size about 5 mm length and 2 mm diameter.

EXAMPLE 7

30 parts (dry weight) of the extruded, wet, immobilised cells obtained in Example 6 were incubated at 20° C. in 1000 parts of an aqueous solution containing 2.75 parts of potassium cyanide at pH 8.5. After 54 minutes the cyanide ion concentration was below 10 ppm. It is seen that, by comparison with Example 3, the activity of the immobilised enzyme was about 6.5% of the activity of the cells prior to immobilisation.

EXAMPLE 8

A sample of the extruded, wet, immobilised cells obtained in Example 6 were dried at 30° C. for 90 minutes. 50 parts of the dried immobilised cells were tested for enzyme activity as in Example 7. The time taken for the cyanide ion concentration to reach 10 ppm was about 65 minutes. It is seen that the activity of the dried cells was about half that of the wet immobilised cells.

EXAMPLE 9

Examples 6 and 7 were repeated, with similar results, using a 1% solution of 'Zetag' 94 (supplied by Allied Colloids Ltd) in place of the 2% solution of 'Primafloc' C7.

EXAMPLE 10

Example 9 was repeated using 'Zetag' 64 in place of 'Zetag' 94. Similar results were obtained.

EXAMPLE 11

Example 6 was repeated and 2 g of the wet, extruded, immobilised cells were packed into a column 9 mm diameter and 15 cm length. A 50 mM aqueous solution of potassium cyanide at pH 8.5 was passed at 20° C. through the column at a rate of 150 ml $hr^{-1}$. The eluent contained 260 ppm of cyanide ions, i.e. about 80% of the cyanide ions had been degraded. After 200 hours the eluent contained about 1200 ppm of cyanide ions.

EXAMPLE 12

Example 11 was repeated at a flow rate of 50 ml $hr^{-1}$. The eluent contained 52 ppm of cyanide ions, i.e. about 96% of the cyanide ions had been degraded. After 200 hours the eluent contained 780 ppm of cyanide ions.

EXAMPLE 13

Example 2 was repeated and 100 parts (dry weight) of the harvested cells were suspended in 1000 parts of 0.1 M Tris. HCl buffer (pH 8.5) at 4° C. To the resultant suspension was added 250 parts of acrylamide, 7 parts of N,N methylene bisacrylamide, 150 parts of 5% N,N,N'N' tetramethylene diamine and 150 parts of 2.5% ammonium persulphate. The mixture was incubated at 37° C. for 5 minutes whereupon a gel formed. When the gel had set it was extruded through a 2 mm aperture and cut into particles as in Example 6. The activity of the immobilised enzyme, tested as described in Example 7, was about 25% of that of the unimmobilised cells.

EXAMPLE 14

Example 2 was repeated and 5 parts (dry weight) of the harvested cells were suspended in 1000 parts of 0.1 M Tris. HCl buffer (pH 8.5). To this suspension was added 20 parts of sodium alginate. The mixture was stirred for 10 minutes and then added dropwise, with stirring, to 10000 parts of 0.2 M calcium chloride made up in Tris. HCl buffer (pH 8.5). The resultant suspension of calcium alginate particles, containing the cells, was stirred for 1 hour and then the particles were harvested by filtration on a Whatman No. 1 filter paper.

The activity of the immobilised cells was assessed as described in Example 7 and found to be about 80% of that of the unimmobilised cells of Example 3.

EXAMPLE 15

A cell suspension of *Mycoleptodiscus terrestris* (CBS 231.58) was prepared from an agar slant and inoculated into 50 ml of medium G and incubated statically at 28° C. for 3 days. 10 ml of the resultant culture was transferred to 2000 ml of medium H in a flask and incubated, with shaking, at 28° C. for 28 hours. The organism grew in the mycelial form.

Cyanide hydratase was then induced by adjusting the pH to 7.5 and adding hydrogen cyanide to a concentration of 1 m Molar and incubating for 12 hours at 28° C.

The mycelium was then harvested by centrifugation at 10000 g for 10 minutes, and then immobilised by the procedure of Example 6 and the activity of the immobilised cells assessed by the procedure of Example 7. The activity was similar to that of the wet, extruded, immobilised *Fusarium moniliforme* cells used in Example 7.

Medium G had the following composition:

| V8 tomato and vegetable juice supernatant | 200 ml |
| --- | --- |
| 50 mM phosphate buffer | 800 ml |

Medium H was the same as medium A except that the amount of KH$_2$PO$_4$ was increased from 5 g to 10 g.

EXAMPLE 16

Example 15 was repeated replacing medium H by
(i) medium C
(ii) medium D
(iii) medium E
(iv) medium F The organism did not grow in medium C and media D, E and F, gave pelleted growth.

EXAMPLE 17

Example 15 was repeated, with similar results, using *Helminthosporium sorghicola* (CBS 249.49) in place of *Mycoleptodiscus terrestris* and using medium A in place of medium H.

We claim:

1. A process for the degradation of inorganic cyanides in effluents comprising contacting an effluent containing cyanide ions at a concentration of at least 50 mM with a fungal mycelium, that has been immobilised by flocculation or entrapment and in which cyanide hydratase has been induced, for sufficient time to degrade at least 95% of the cyanide ions in the effluent, said fungal mycelium being a mycelium of a fungus selected from *Stemphylium loti, Mycoleptodiscus terrestris, Fusarium moniliforme, Helminthosporium sorghicola,* and *Gloecercospora sorghi.*

2. A process according to claim 1 wherein the immobilised fungal mycelium is obtained by adding a polyelectrolyte flocculating agent to a fungal mycelium in which cyanide hydratase has been induced.

3. A process according to claim 1 wherein the immobilised fungal mycelium is obtained by adding a mixture of the fungal mycelium, in which cyanide hydratase has been induced, and a solution of an aliginate to a precipitant for the alginate.

4. A process according to claim 2 or claim 3 in which the effluent is treated at 0°–30° C.

5. A process according to claim 1 in which the effluent is treated at a pH of 7–10.

6. A process according to claim 1 in which the effluent is treated for sufficient time to degrade at least 98% of the cyanide ions in the effluent.

* * * * *